United States Patent
Birkhold (10) Patent No.: US 12,303,318 B1
(45) Date of Patent: May 20, 2025

(54) COMPUTER-IMPLEMENTED METHOD FOR DETERMINING SPATIALLY RESOLVED RADIATION EXPOSURE INFORMATION, X-RAY DEVICE, COMPUTER PROGRAM, AND ELECTRONICALLY READABLE DATA STORAGE MEDIUM

(71) Applicant: Siemens Healthineers AG, Forchheim (DE)

(72) Inventor: Annette Birkhold, Stuttgart (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/921,229

(22) Filed: Oct. 21, 2024

(30) Foreign Application Priority Data

Nov. 2, 2023 (DE) ..................... 10 2023 210 869.0

(51) Int. Cl.
    *A61B 6/00* (2024.01)
    *A61B 6/40* (2024.01)

(52) U.S. Cl.
    CPC ............ *A61B 6/542* (2013.01); *A61B 6/4035* (2013.01)

(58) Field of Classification Search
    CPC .............................. A61B 6/542; A61B 6/4035
    See application file for complete search history.

(56) References Cited

U.S. PATENT DOCUMENTS

| 2012/0148017 A1* | 6/2012 | Takahashi | A61B 6/4035 378/42 |
|---|---|---|---|
| 2016/0196406 A1 | 7/2016 | Fält et al. | |
| 2017/0095223 A1 | 4/2017 | Tian | |

FOREIGN PATENT DOCUMENTS

JP      2004065815 A      3/2004

\* cited by examiner

*Primary Examiner* — Courtney D Thomas
(74) *Attorney, Agent, or Firm* — Lempia Summerfield Katz LLC

(57) ABSTRACT

A computer-implemented method for determining spatially resolved radiation exposure information for a patient during an examination by an imaging X-ray device includes: determining preliminary dose information, when a compensating filter is used that is arranged between the patient and the X-ray tube unit in the X-ray field and causes an inhomogeneous dose distribution in the plane perpendicular to a central ray of the X-ray field; calculating dose distribution information using the preliminary dose information, which specifies at least the dose distribution of the X-ray dose acting on the patient in the portion of the X-ray field covered by the compensating filter, by a filter model that uses at least one filter parameter specifying the compensating filter and its arrangement in the X-ray field; and determining the patient entrance dose information using the dose distribution information.

17 Claims, 5 Drawing Sheets

FIG 7

COMPUTER-IMPLEMENTED METHOD FOR DETERMINING SPATIALLY RESOLVED RADIATION EXPOSURE INFORMATION, X-RAY DEVICE, COMPUTER PROGRAM, AND ELECTRONICALLY READABLE DATA STORAGE MEDIUM

The present patent document claims the benefit of German Patent Application No. 10 2023 210 869.0, filed Nov. 2, 2023, which is hereby incorporated by reference in its entirety.

TECHNICAL FIELD

The disclosure relates to a computer-implemented method for determining spatially resolved radiation exposure information for a patient during an examination by an imaging X-ray device, which has an X-ray tube unit for emitting an X-ray field for the examination, wherein patient entrance dose information, which specifies the X-ray dose acting on the patient, is determined, from which the radiation exposure information is determined. The disclosure also relates to an X-ray device, to a computer program, and to an electronically readable data storage medium.

BACKGROUND

In imaging X-ray devices, X-ray radiation is used to X-ray objects under examination, in particular patients. Because X-ray radiation may have an ionizing effect, the radiation exposure of the patient may be determined, logged, and/or documented. For this purpose, it is known to determine an X-ray dose acting on the patient in order to determine, for example using a patient model, radiation exposure information. The radiation exposure information may include a skin dose and/or an organ dose, (e.g., a spatially resolved skin dose and/or organ dose). It is also known to determine local peak-values of the radiation exposure.

In order to determine patient entrance dose information specifying the X-ray dose acting on the patient, it is known to use measuring devices, which may be arranged as the last component in the beam path before the patient (except for patient positioning means, if applicable). What is known as a DAP chamber, for measuring a dose area product (DAP), is normally employed here as the measuring device, located after the X-ray tube unit, a beam-forming apparatus and, if used, a radiation-filtering apparatus. The dose area product is a radiation quantity that assumes a homogeneous distribution of the X-ray dose.

Because DAP chambers and other measuring devices may cause unwanted scattered radiation, are expensive and take up installation space, it has also been proposed, for example, by the subsequently published European patent application 23197942.8, to provide a kind of virtual measuring device by using an estimation model to calculate the radiation quantity.

While many apparatuses that affect the X-ray radiation of the X-ray field, for instance beam-forming apparatuses, which define the geometry of the X-ray field (for example collimators or other restricting apparatuses), and radiation-filtering apparatuses, which attenuate homogeneously and affect the spectrum, for example, preserve a homogeneous dose distribution perpendicular to the central ray, for which apparatuses the spatial distribution of the dose is specified sufficiently accurately by a radiation quantity such as the dose area product, for instance, there are also radiation-filtering apparatuses known that lead to a spatially inhomogeneous dose distribution in the plane perpendicular to the central ray of the X-ray field. Such radiation-filtering apparatuses are referred to below also as compensating filters.

The use of different materials and/or different attenuation lengths means that compensating filters may lead to inhomogeneity in the spatial distribution of the dose after being traversed. A known example of such compensating filters are what are known as wedge filters, which have a thickness, and hence attenuation length, which increases towards one side. In other words, a semi-transparent compensating filter blocks the X-ray radiation by a different amount at different points, resulting in an inhomogeneous X-ray field.

Present-day methods for determining radiation quantities, (e.g., DAP chambers and virtual measuring apparatuses), do not take the inhomogeneity into account. This may lead to the radiation exposure information for the patient being incorrect because the X-ray dose may be higher locally than assumed on the basis of the radiation quantity, for instance the dose area product.

SUMMARY AND DESCRIPTION

Therefore, the object of the disclosure is to define a way of determining radiation exposure information for a patient more accurately.

This object is achieved by a computer-implemented method, an X-ray device, a computer program, and an electronically readable data storage medium as described herein. The scope of the present disclosure is defined solely by the appended claims and is not affected to any degree by the statements within this summary. The present embodiments may obviate one or more of the drawbacks or limitations in the related art.

In certain examples, when a compensating filter is used that is arranged between the patient and the X-ray tube unit in the X-ray field and causes an inhomogeneous dose distribution in the plane perpendicular to a central ray of the X-ray field, the method may include determining preliminary dose information, which specifies a homogeneously distributed X-ray dose acting on the patient in the absence of the compensating filter. The method may further include calculating dose distribution information, using the preliminary dose information, which specifies at least the dose distribution of the X-ray dose acting on the patient in the portion of the X-ray field covered by the compensating filter, wherein the dose distribution information is calculated by a filter model, which uses at least one filter parameter specifying the compensating filter and its arrangement in the X-ray field. The method may further include determining the patient entrance dose information using the dose distribution information.

In the context of the present disclosure, the preliminary dose information expediently includes a radiation quantity, which may include a dose area product and/or a kerma and/or a variable that depends on the dose area product and/or the kerma. The patient entrance dose information may also be expressed by such radiation quantities, in particular then spatially resolved.

It is proposed to determine an inhomogeneous dose distribution perpendicular to the central ray by applying a filter model, into which is input in particular at least the geometry and/or the at least one material of the compensating filter, in particular wedge filter, and the preliminary dose information. As presented in greater detail below, the dose distribution information may already state the spatially resolved dose in absolute terms but may also contain just the relative dose values as a pure distribution.

From the dose distribution information may be determined the patient entrance dose information, if applicable presented in combination with the preliminary dose information and/or, depending on the embodiment, further information. As a result of the dose distribution information, which specifies the dose distribution, the patient entrance dose information is likewise spatially resolved and specifies the inhomogeneity resulting from the compensating filter.

Hence, it is possible to take adequate account of inhomogeneities caused by compensating filters when estimating the radiation exposure information for the patient. In particular, local X-ray doses, (e.g., peak skin doses or organ doses), are not underestimated. The actual radiation exposure of the patient is determined significantly more accurately.

The compensating filter may be a wedge filter. The wedge filter may be made of a metal, e.g., aluminum.

Designs are conceivable in which the wedge filter does not cover the entire X-ray field perpendicular to the direction of the central ray. In certain examples, in order to determine the patient entrance dose information in a portion of the X-ray field not covered by the compensating filter, the preliminary dose information is applied for this portion. Thus, in the region that the compensating filter does not cover, i.e., where it has no effect on the X-ray field, it is possible to set the dose, for instance a dose area product, specified by the preliminary dose information, which relates to the situation without compensating filter. The dose distribution information is then applied for the remaining region, which is covered by the compensating filter, in order to determine the rest of the patient entrance dose information.

Various specific embodiments are conceivable depending on whether a measuring device is present. These embodiments take into account that although a measuring device, (e.g., a DAP chamber), is located after the compensating filter in the beam direction, the distribution of the X-ray dose is assumed to be homogeneous perpendicular to the central ray. Nonetheless, a measurement by a measuring device may be employed expediently as part of the present disclosure.

For instance, the X-ray device may have a measuring device for measuring a total dose, in particular a dose area product, which measuring device follows, in the direction towards the patient, the compensating filter in the X-ray field, and by which is determined total dose information, which is used in determining the patient entrance dose information. As the measuring device, it is possible to use a DAP chamber that may be present anyway. The total dose information provides further useful information, which may further increase the quality of the ascertainment of the radiation exposure information. The total dose information may be employed in various ways.

For instance, filter dose information, which specifies the total filter dose to be distributed inhomogeneously in the portion of the X-ray field covered by the compensating filter, may be determined from the total dose information. When the compensating filter completely covers the x-ray field, the total dose information already equals the filter dose information, because the total dose information is the homogeneously redistributed dose of the inhomogeneous dose distribution. When the compensating filter does not entirely cover the X-ray field, the filter dose information may be determined expediently by subtracting a patient entrance dose, which was determined as the patient entrance dose information for the portion not covered by the compensating filter, from the total dose specified by the total dose information.

The filter dose information may be used as an input variable for the filter model, where the dose distribution information specifies the absolute dose level directly, or initially a dose distribution stating just relative dose levels is determined and is applied by the filter model to distribute the total filter dose of the filter dose information. In other words, the filter model may implicitly perform the distribution of the dose that remains after passage through the compensating filter. It is also conceivable, however, that initially a dose distribution stating just relative dose levels is determined, on the basis of which the filter model distributes the total filter dose of the filter dose information in order to determine absolute dose levels. In this case, the relative dose levels therefore specify solely the inhomogeneity caused by the compensating filter, hence relative dose levels. The total filter dose is then used for the correct normalization in order to obtain the absolute dose levels in a spatially dependent manner. In both cases, the absolute dose levels in the portion of the X-ray field covered by the compensating filter augment, if this portion does not cover the entire X-ray field, the total dose of the preliminary dose information set for the uncovered portion of the X-ray field; if the compensating filter fully covers the X-ray field, the patient entrance dose information is defined solely by the dose distribution containing the absolute dose levels, e.g., by the dose distribution information.

Alternatively, as part of the method, the filter dose information may be used to check the plausibility of the dose distribution information. The dose distribution information, again containing absolute dose levels, is determined in this case, from which it is possible accordingly to determine an expected total filter dose, which may be compared with the total filter dose according to the filter dose information, and which should be equal thereto in the case of plausibility. In the event of deviations, a correction and/or recalculation may be made.

When the filter model outputs absolute dose levels in the dose distribution, it may be assumed that the X-ray dose according to the preliminary dose information is the X-ray radiation incident on the compensating filter. This is then attenuated by the compensating filter in a manner specified by the filter model, accordingly in a spatially dependent manner.

In summary, the preliminary dose information may be determined such that it takes into account all the apparatuses in the beam path that leave the dose distribution homogeneous and that are also used in the examination. Such apparatuses that leave the dose distribution homogeneous may include another radiation-filtering apparatus, (e.g., for adapting the X-ray spectrum), and/or a beam-forming apparatus, (e.g., a collimator), and/or other restricting apparatus.

While the preliminary dose information may be measured before inserting the compensating filter in the beam path, the preliminary dose information may alternatively be determined by an estimation model, which uses input data including at least one operating parameter of the X-ray tube unit to determine output data including the preliminary dose information, and which is configured on the basis of measurement data for the homogeneously distributed X-ray dose acting on a patient in the absence of the compensating filter. As already described, a measuring device, in particular a DAP chamber, may be used here to measure measurement data. In a development, the estimation model may also include a trained estimation function, e.g., an algorithm trained by machine learning.

In particular, the estimation model may be determined in which the estimation model is introduced as a model that has been refined (from a base model). The disclosure in this application relating to determining and applying the estimation model/refined model is hereby included in full in this disclosure by reference.

As already mentioned, the filter parameters may specify particularly advantageously the geometry and/or the at least one material of the compensating filter. In addition, the filter parameters may specify the position and orientation, which may also be used beforehand for identifying portions that are, and are not, covered by the compensating filter. In other words, at least one geometry parameter specifying the geometry of the compensating filter and/or at least one material parameter specifying the material of the compensating filter and/or at least one position parameter specifying the position and/or orientation of the compensating filter in the X-ray field may be used as the filter parameter. For example, it may be declared by a user, or identified automatically, which compensating filter is deployed in which position and orientation. Additionally, for different available compensating filters, at least some of the filter parameters, (e.g., filter parameters specifying geometry and material), may be retrieved from a database by a computing device performing the method, (e.g., by a control device of the X-ray device).

In a specific design of the filter model, the filter model may be an analytical physical model. This means in particular that the dose distribution information may be calculated on the basis of physical laws, in particular specified by at least one formula. Assumptions may also be made here, for instance that there is no aging present, the material is homogeneous, there is no scattered radiation, and such like. For example, the analytical model may use transmission lengths, in particular a thickness of the compensating filter, and/or attenuation coefficients, in particular based on the material of the compensating filter, to calculate respective attenuations for partial beams of the X-ray field. This means that fundamentally known physical relationships may be used that specify the attenuation behavior of X-ray radiation when passing through matter. Excellent results may thereby be achieved just on physical principles, in particular depending on specifically made assumptions.

Alternatively, or additionally, the filter model may include a simulation model for performing a physical simulation. In this case, fundamentally known physical simulation methods are used to achieve a highly accurate calculation of the interaction between X-ray radiation and the filter material, in particular taking into account physical effects for which assumptions would be made in purely analytical modeling. The simulation may include a finite element simulation and/or a Monte Carlo simulation. Simulations that may be carried out quickly may be employed here, for instance, fast Monte Carlo simulations.

Alternatively, or additionally, the filter model may include a trained filter model function, e.g., a filter model algorithm trained by machine learning. Trained functions may be characterized by very short run times, and therefore the learned physical correlations may be used in an extremely time-efficient manner to determine the dose distribution information. In certain examples, the trained filter model function may include a convolutional neural network (CNN), e.g., a two-dimensional U-net.

The trained filter model function may be trained on the basis of measurement data measured in a spatially resolved manner in particular by an X-ray film and/or an X-ray detector. Specific measurement methods, in particular X-ray films and/or X-ray detectors, may be employed here in order to establish, in a spatially resolved manner, the actual X-ray dose distribution after the previously homogeneously distributed X-ray radiation has passed through the compensating filter, and to use this as the training data. It is also conceivable to employ, alternatively or additionally, simulation results for training the filter model function. Additional physical effects, which would be covered by assumptions in analytical approaches and also in some physical simulations, may be taken into account by a suitably expanded choice of input data.

In certain examples, a trained function models cognitive functions that humans associate with other human brains. As a result of training based on training data (machine learning), the trained function is capable of adapting to new circumstances and detecting and extrapolating patterns.

In certain examples, parameters of a trained function may be configured by training. In particular, supervised learning, semi-supervised learning, unsupervised learning, reinforcement learning, and/or active learning may be used. Furthermore, representation learning (also known as feature learning) may also be employed. The parameters of the trained function may be configured iteratively by a plurality of training steps.

A trained function may include a neural network, a support vector machine (SVM), a decision tree, and/or a Bayes network, and/or the trained function may be based on k-means clustering, Q-learning, genetic algorithms, and/or association rules. In particular, a neural network may be a deep neural network, a convolutional neural network (CNN), or a deep CNN. In addition, the neural network may be an adversarial network, a deep adversarial network, and/or a generative adversarial network (GAN).

For the purpose of determining the radiation exposure information, the radiation exposure information may be determined using a patient model positioned virtually in the X-ray field and/or including a spatially resolved skin dose value and/or at least one organ dose value and/or at least one item of scattered-radiation information. Fundamentally known methods may be employed here to determine the radiation exposure information when the spatial distribution is known according to the patient entrance dose information. The dose distribution is finally forward-projected onto the patient, in particular, by a patient model. It is also possible to take into account patient positioning means, for example, the attenuation properties of a patient table and/or a mattress. In addition, the determining of the radiation exposure information may take into account the transition from air to skin and/or scattered radiation. It is hence possible to determine finally, for example, a skin dose distribution, an organ dose distribution, a scattered-radiation dose distribution and such like.

In addition to the method, the disclosure also relates to an imaging X-ray device, which has an X-ray tube unit having an optionally usable compensating filter, which brings about an inhomogeneous dose distribution in the plane perpendicular to a central ray of the X-ray field, an X-ray detector, and a control device, which is configured to perform a method as claimed in one of the preceding claims. All the statements relating to the method may be applied analogously to the X-ray device, and vice versa, and therefore the aforementioned advantages may likewise be achieved by the X-ray device.

The X-ray device may also include, (like the compensating filter located after the X-ray tube unit in the beam path), a further radiation-filtering apparatus and/or a beam-forming apparatus. In addition, a measuring device, (e.g., a DAP chamber), may be provided. The X-ray device may be an X-ray device having a C-arm, on which the X-ray tube unit and the X-ray detector are arranged opposite one another. The patient may be supported on a patient table, for example.

The control device, which may have at least one processor and/or at least one storage means, may have functional units formed by hardware and/or software for performing parts of the method. In addition to an acquisition unit, which may control the acquisition operation of the X-ray device, the control device may include a first determination unit for determining, in the case when the compensating filter, arranged between the patient and the X-ray tube unit in the X-ray field, is used, preliminary dose information, which specifies a homogeneously distributed X-ray dose acting on the patient in the absence of the compensating filter. The control device may further include a calculation unit for calculating by a filter model, which uses at least one filter parameter specifying the compensating filter and its arrangement in the X-ray field, and using the preliminary dose information, dose distribution information, which specifies at least the dose distribution of the X-ray dose acting on the patient in the portion of the X-ray field covered by the compensating filter. The control device may further include a second determination unit for determining patient entrance dose information, which specifies the X-ray dose acting on the patient, using the dose distribution information. The control device may further include a third determination unit for determining radiation exposure information for the patient from the patient entrance dose information.

Further functional units may also be provided for realizing further, in particular optional, acts.

A computer program may be loaded directly into a storage device or component of a computing device, (e.g., a control device of an X-ray device), and includes program means that, when the computer program is executed on the computing device, cause this to perform the acts of a method as disclosed herein. The computer program may be stored on an electronically readable data storage medium, which therefore includes control information stored thereon that includes at least one computer program and is configured such that when the data storage medium is used in a computing device, in particular a control device of a magnetic resonance device, this computing device is designed to perform a method as disclosed herein. The data storage medium may be in particular a non-transient data storage medium, for instance a CD-ROM.

BRIEF DESCRIPTION OF THE DRAWINGS

Further advantages and details of the present disclosure are presented in the embodiments described below and with reference to the drawings, in which.

DETAILED DESCRIPTION

Figure 1:
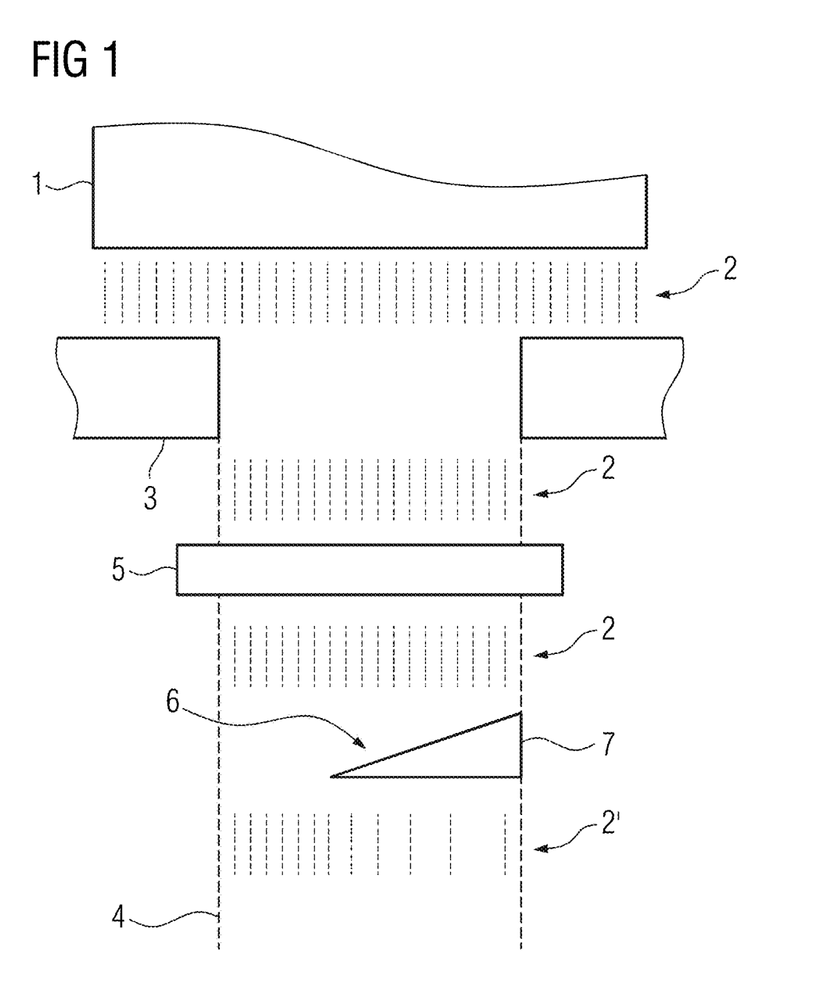
FIG. 1 depicts an example of an outline for explaining the origins of an inhomogeneous distribution of an X-ray dose.

FIG. 1 is a schematic outline relating to producing an X-ray field having an X-ray dose (patient entrance dose), to which a patient is exposed for the purpose of an imaging examination by an X-ray device in order to determine an X-ray image by X-raying. For better illustration, a parallel-beam geometry is indicated here instead of a cone-beam geometry, as is used more frequently; the statements may of course be applied correspondingly to a cone-beam geometry.

An X-ray tube unit 1, (e.g., an X-ray tube), generates X-ray radiation. Perpendicular to the exit direction, the X-ray dose is evenly distributed, i.e., homogeneously distributed, which is indicated by the schematic equally spaced X-rays 2. This also does not change when using a beam-forming apparatus 3, for instance a collimator, which defines the extent of the X-ray field 4 to be used for the imaging examination. In addition, a radiation-filtering apparatus 5, which does not affect the homogeneous distribution of the X-ray dose, may optionally be used, for instance for adapting the spectrum of the X-ray radiation. Even after passing through the radiation-filtering apparatus 5, the distribution of the X-ray dose is homogeneous, which is indicated schematically by the X-rays 2 still being equally spaced.

If now, however, a wedge filter 5 is used an example of a compensating filter 6, which attenuates the X-ray radiation in a spatially dependent manner, in the present case as a result of the wedge shape, an inhomogeneous distribution of the X-ray dose is produced in the plane perpendicular to the beam direction (direction of the central ray), as shown by the X-rays 2', which, again shown schematically, are spaced further apart at greater thicknesses of the wedge filter 7.

If a DAP chamber were to be arranged as a measuring device after the arrangement shown in FIG. 1, this would output a single measurement value for the dose area product or another radiation quantity, i.e., would not take account of the inhomogeneous distribution of the X-ray dose, which also applies to spatially resolved radiation exposure information derived therefrom for the patient. In particular, local X-ray doses may be underestimated.

In order to improve the determining of the radiation exposure information, which determining takes into account the inhomogeneous dose distribution, in the exemplary embodiments now presented of the method, the patient entrance dose information, which specifies the X-ray dose (patient entrance dose) acting on the patient, is determined, taking into account the inhomogeneity of the distribution, i.e., as a dose distribution containing absolute dose levels.

Figure 2:
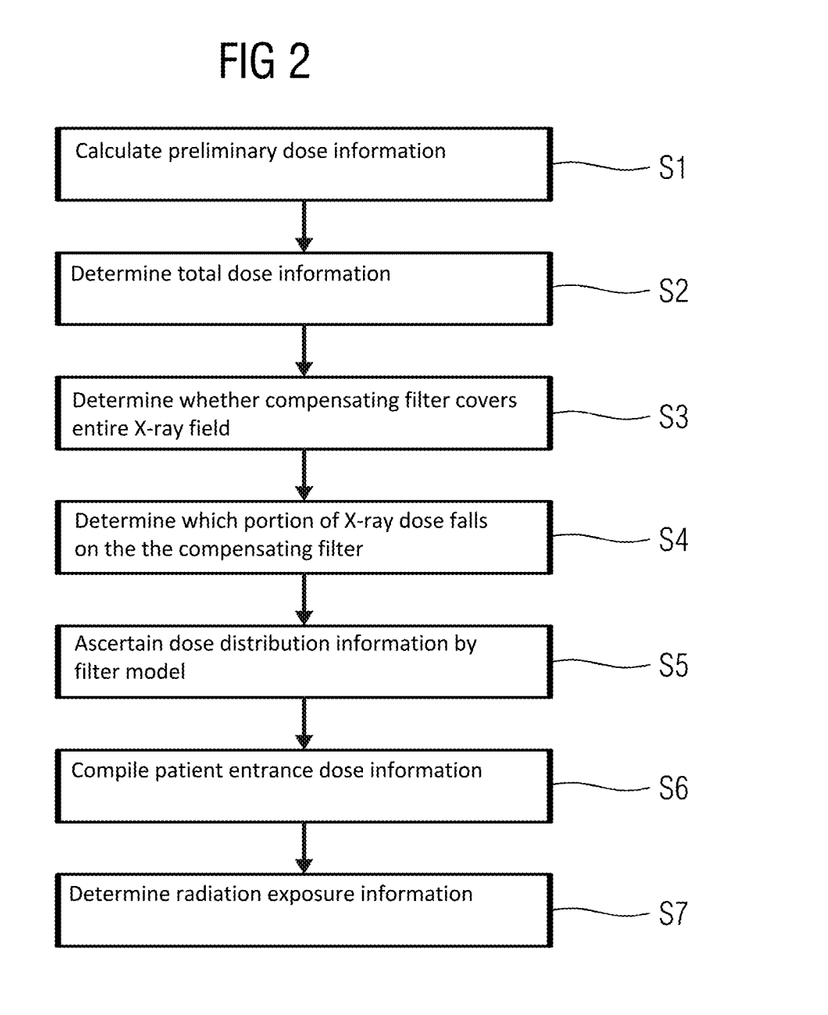
FIG. 2 depicts a flow diagram of a first embodiment of the method.

FIG. 2 shows a flow diagram of a first exemplary embodiment of the method. Initially, in act S1, an estimation model calculates preliminary dose information. Assuming a homogeneous distribution of the X-ray dose, the preliminary dose information may be determined as a single radiation quantity, in particular a dose area product. The preliminary dose information specifies the homogeneously distributed X-ray dose that would act on the patient if the compensating filter 6 were not used. It takes into account all the other potentially used apparatuses, thus in particular the beam-forming apparatus 3 and the radiation-filtering apparatus 5, if used.

In act S2, total dose information which specifies the total dose before acting on the patient assuming a homogeneous distribution of the X-ray dose, is determined by a measuring device, in particular a DAP chamber. The total dose information may likewise be determined as a radiation quantity, in particular in the case of a DAP chamber as a dose area product. The total dose information thus just states the total dose that exists without taking into account the effects of the compensating filter 6.

In act S3, it is determined from the position and orientation of the compensating filter 6 in the X-ray field 4 whether the compensating filter 6 covers the entire X-ray field 4 perpendicular to the direction of the central ray, or whether a portion is not covered. If a portion of the X-ray field 4 is not covered by the compensating filter 6, it is already possible to determine part of the patient entrance dose information, namely as the X-ray dose in the uncovered portion, which dose is specified by the preliminary dose information, because of course no change to inhomogeneity takes place here. Thus, in particular, the dose area product defined as the preliminary dose information may be set for the uncovered portion.

Figure 3:
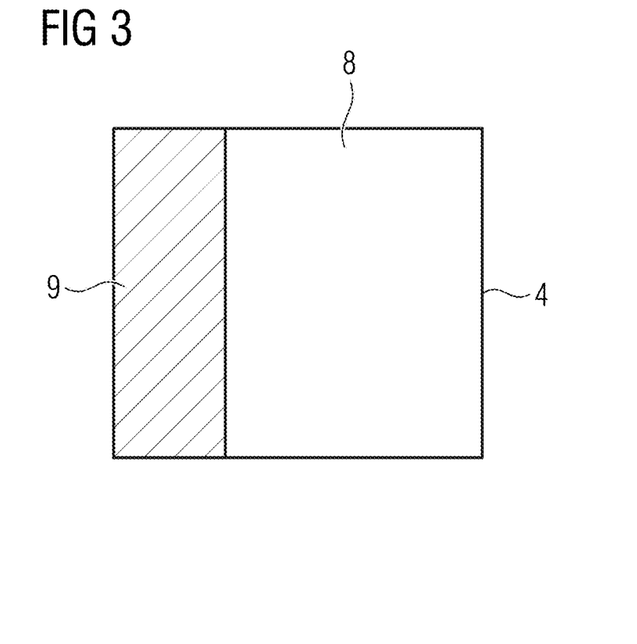
FIG. 3 depicts an example of an outline of portions of the X-ray field.

FIG. 3 explains, in a graphical manner, the situation already indicated in FIG. 1, in which only a first portion 8 of the X-ray field 4 is covered in the plane perpendicular to the direction of the central ray by the compensating filter 6, here the wedge filter 7. The remaining, second portion 9 is thus not covered by the compensating filter 6. Here, the distribution of the dose remains in particular homogeneous.

In act S4, likewise in the case in which the X-ray field 4 is not entirely covered by the compensating filter 6, is determined what portion of the X-ray dose specified by the preliminary dose information actually falls on the compensating filter 6 or is affected thereby. Thus filter dose information is ascertained that specifies a total filter dose, the distribution of which is made inhomogeneous by the compensating filter 6. The total filter dose is determined here by subtracting from the total dose of the total dose information the X-ray dose administered for the portion 9 of the X-ray field 4 that is not covered by the compensating filter 6.

In act S5, a filter model is used in order to ascertain dose distribution information that specifies what inhomogeneous distribution of the dose is produced by the compensating filter 6. The filter model uses here as an input variable at least one filter parameter, (e.g., a plurality of filter parameters), which specifies the geometry (i.e., geometry parameter), the at least one material (i.e., material parameter), and the position and orientation (i.e., position parameter) of the compensating filter 6 in the X-ray field 4. The filter model may include an analytical physical model and/or a physical simulation model and/or a trained filter model function. In the case of a trained filter model function, this may include a two-dimensional U-net and/or may be trained on the basis of simulated training data or training data derived from measurement data. In the case of a simulation model, which performs a physical simulation, the physical simulation may be a fast Monte Carlo simulation.

The total filter dose, which was determined in act S4, may already be input to the filter model as the X-ray dose that is to be distributed inhomogeneously. Alternatively or additionally, however, it is also conceivable that the filter model works on the basis of the preliminary dose information, which, of course, describes the amount of X-ray dose incident on the compensating filter 6 and that is attenuated here in a spatially inhomogeneous manner. If the preliminary dose information specifying the dose incident on the compensating filter 6 is not used directly, a dose distribution containing relative dose levels may be determined first, which the filter model then applied to the total filter dose to be distributed, in order to determine the absolute dose levels. In all cases, the dose distribution information expediently already contains absolute dose levels in the dose distribution.

Something that the flow diagram does not present in greater detail is that the filter dose information may also be employed for checking the plausibility of the result of the filter model, i.e., the dose distribution information. If the dose distribution information is determined solely on the basis of the preliminary dose information, the total filter dose remaining overall after the compensating filter 6 still equals the total filter dose based on the filter dose information. If this is not the case, then implausibility exists, and a recalculation, correction, or such like may be made.

In act S6, the patient entrance dose information is then compiled, either, in the case that the compensating filter 6 covers the X-ray field 4 in full, as the dose distribution information, or as the dose distribution information in the covered portion 8 and the X-ray dose based on the preliminary dose information in the portion 9 (see act S3).

Finally, this now spatially resolved patient entrance dose information, more precisely the patient entrance dose specified thereby in terms of its spatial distribution, is used in act S7 to determine therefrom the radiation exposure information for the patient. For this purpose, the patient entrance dose is forward-projected onto a patient model positioned virtually in the X-ray field 4, of course with the possibility of taking into account, if necessary, properties of patient positioning means, the air-skin interface and/or scattered radiation effects, as is fundamentally known in the prior art. The radiation exposure information may contain, for example, a skin dose, an organ dose and/or scattered radiation information.

Figure 4:
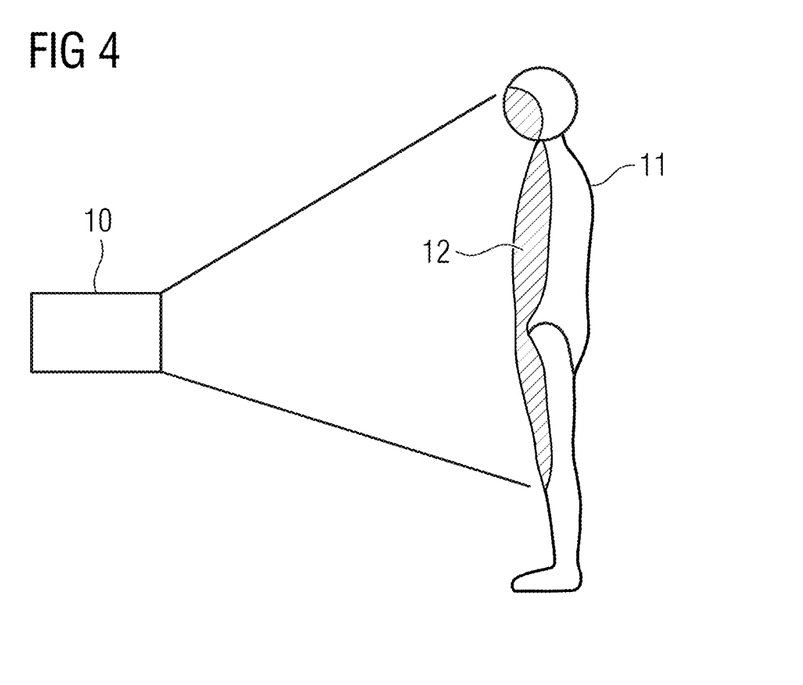
FIG. 4 depicts an example of an outline relating to determining radiation exposure information.

FIG. 4 explains by way of example how the patient entrance dose 10 is forward-projected onto the virtual patient model 11, and which regions 12 of the patient are particularly affected.

Figure 5:
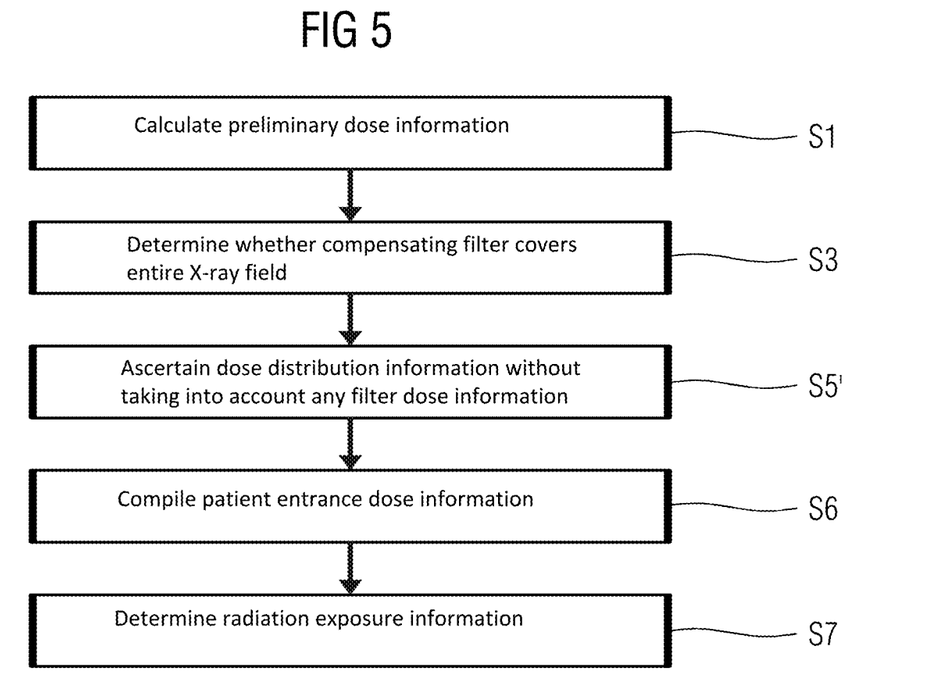
FIG. 5 depicts a flow diagram of a second embodiment of the method.

FIG. 5 shows a flow diagram of a second exemplary embodiment of the method, in which a measuring device is omitted. This means in particular that now solely the preliminary dose information is used, which is again determined in act S1. As before, act S3 likewise checks whether there is a portion 8 of the X-ray field 4 that is not covered by the compensating filter 6, for which portion again the preliminary dose information may be applied directly.

In act S5', the filter model is used on the basis of the filter parameters and the preliminary dose information without taking into account any filter dose information in order to ascertain the dose distribution information and thereby compile, in act S6, the patient entrance dose information in an analogous way to the first exemplary embodiment. Act S7 is also carried out in an analogous way to the first exemplary embodiment.

Figure 6:
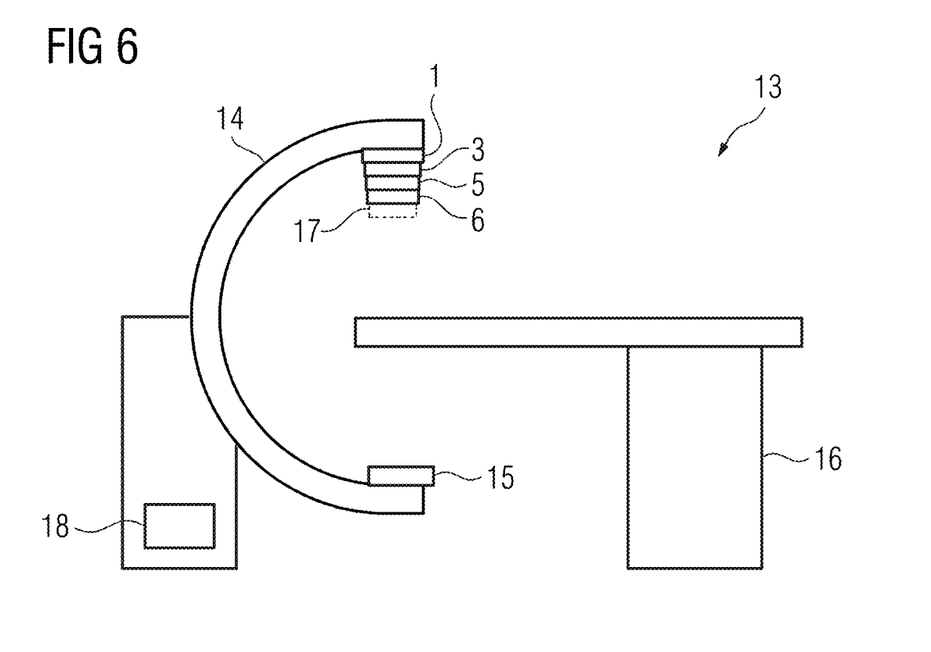
FIG. 6 depicts an example of an X-ray device.

FIG. 6 shows a schematic outline of an exemplary embodiment of an X-ray device 13, which in the present case has a C-arm 14 by way of example, on which the X-ray tube unit 1 and the X-ray detector 15 are arranged opposite one another. The C-arm 14 may move, in particular may pivot about different rotational axes, about a patient table 16, on which the patient may be positioned.

Other embodiments of the X-ray device 13 are also conceivable, for instance in the form of a computed tomography device, radiography device and such like.

FIG. 6 shows as part of a tube unit arrangement, which also includes the X-ray tube unit 1, the beam-forming apparatus 3, the radiation-filtering apparatus 5, and the compensating filter 6. The optional measuring device 17 is indicated merely by dashed lines.

Figure 7:
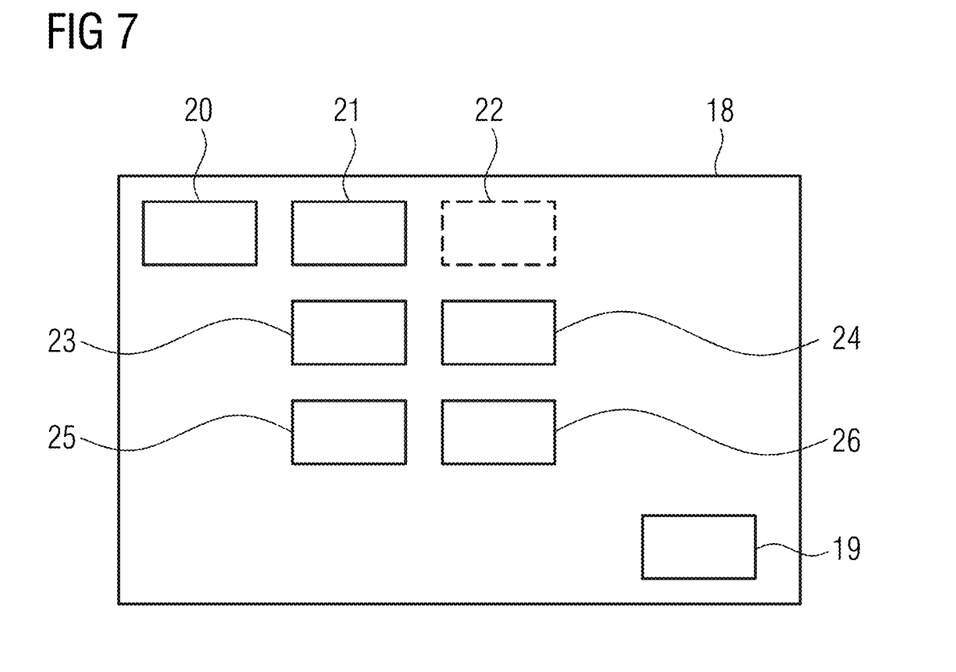
FIG. 7 depicts an example of a functional design of a control device of the X-ray device.

The operation of the X-ray device 13 is controlled by a control device 18, which is also designed to implement the method described here, and the functional design of which is explained in greater detail by FIG. 7.

According to the figure, the control device 18 includes a storage device or component 19, in which it is possible to store a variety of information processed by the method in addition to acquired X-ray data or X-ray images. For the purpose of controlling the acquisition operation, the control device 18 additionally has an acquisition unit 20, as is fundamentally known.

In a first determination unit 21, it is possible to determine the preliminary dose information, as described above in accordance with act S1. An optional measuring and processing unit 22 controls, if present, the measuring device 17 for determining the total dose information (act S2) and may also determine the filter dose information in accordance with act S4.

In an assignment unit 23, it is possible to check, in accordance with act S3, whether the compensating filter 6 in its relevant position and orientation covers the entire X-ray field 4, or whether an uncovered portion 9 exists. In addition, the preliminary dose information may be suitably applied in this portion 9.

In a calculation unit 24, the filter model is applied in accordance with act S5, with the patient entrance dose information then being compiled in a second determination unit 25, in accordance with act S6. A third determination unit 26 uses this patient entrance dose information to determine the radiation exposure information in accordance with act S7.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for determining spatially resolved radiation exposure information for a patient during an examination by an imaging X-ray device comprising an X-ray tube unit for emitting an X-ray field for the examination, wherein patient entrance dose information, which specifies an X-ray does acting on the patient, is determined, from which the radiation exposure information is determined, the method comprising:

determining preliminary dose information that specifies a homogeneously distributed X-ray dose acting on the patient in an absence of a compensating filter arranged between the patient and the X-ray tube unit in the X-ray field that is configured to cause an inhomogeneous dose distribution in a plane perpendicular to a central ray of the X-ray field;

calculating dose distribution information using the preliminary dose information, wherein the dose distribution information specifies at least a dose distribution of an X-ray dose acting on the patient in a portion of the X-ray field covered by the compensating filter, and wherein the dose distribution information is calculated by a filter model that uses at least one filter parameter specifying the compensating filter and an arrangement of the compensating filter in the X-ray field; and determining the patient entrance dose information that specifies the X-ray dose acting on the patient using the dose distribution information.

2. The method of claim 1, wherein, in order to determine the patient entrance dose information in a portion of the X-ray field not covered by the compensating filter, the preliminary dose information is applied.

3. The method of claim 1, wherein the imaging X-ray device further comprises a measuring device for measuring a total dose,
wherein the measuring device follows, in a direction towards the patient, the compensating filter in the X-ray field,
wherein total dose information is determined using the measuring device, and
wherein the total dose information is used in the determining of the patient entrance dose information.

4. The method of claim 3, wherein filter dose information, which specifies a total filter dose to be distributed inhomogeneously in the portion of the X-ray field covered by the compensating filter, is determined from the total dose information.

5. The method of claim 4, wherein the filter dose information is used as an input variable for the filter model,
wherein the dose distribution information specifies an absolute dose level directly, or initially a dose distribution stating just relative dose levels is determined and is applied by the filter model to distribute the total filter dose of the filter dose information.

6. The method of claim 4, wherein the filter dose information is used for checking a plausibility of the dose distribution information.

7. The method of claim 4, wherein the filter dose information is determined when the compensating filter does not entirely cover the X-ray field by subtracting a patient entrance dose determined for the portion not covered by the compensating filter from the total dose specified by the total dose information.

8. The method of claim 3, wherein the total dose is a dose area product.

9. The method of claim 1, wherein the preliminary dose information is determined by an estimation model, which uses input data comprising at least one operating parameter of the X-ray tube unit (1) to determine output data comprising the preliminary dose information, and which is configured based on measurement data for the homogeneously distributed X-ray dose acting on the patient in the absence of the compensating filter.

10. The method of claim 1, wherein the filter parameter comprises at least one geometry parameter specifying a geometry of the compensating filter, at least one material parameter specifying a material of the compensating filter, at least one position parameter specifying a position and/or orientation of the compensating filter in the X-ray field, or a combination thereof.

11. The method of claim 1, wherein the filter model comprises an analytical physical model and/or a simulation model for performing a physical simulation.

12. The method of claim 1, wherein the filter model comprises a trained filter model function.

13. The method of claim 12, wherein the trained filter model function comprises a convolutional neural network, and/or
wherein the trained filter model function is trained based on measurement data measured in a spatially resolved manner by an X-ray film and/or an X-ray detector.

14. The method of claim 13, wherein the convolutional neural network is a two-dimensional U-net.

15. The method of claim 1, wherein the spatially resolved radiation exposure information is determined using a patient model positioned in the X-ray field, and/or
wherein the spatially resolved radiation exposure information comprises a spatially resolved skin dose value, at least one organ dose value, at least one item of scattered-radiation information, or a combination thereof.

16. An X-ray device comprising:
an X-ray tube unit having an optionally usable compensating filter, which brings about an inhomogeneous dose distribution in a plane perpendicular to a central ray of an X-ray field emitted by the X-ray tube unit;
an X-ray detector; and
a control device configured to:
determine preliminary dose information that specifies a homogeneously distributed X-ray dose acting on a patient in an absence of the compensating filter;
calculate dose distribution information using the preliminary dose information, wherein the dose distribution information specifies at least a dose distribution of an X-ray dose acting on the patient in a portion of the X-ray field covered by the compensating filter, and wherein the dose distribution information is calculated by a filter model that uses at least one filter parameter specifying the compensating filter and an arrangement of the compensating filter in the X-ray field; and
determine patient entrance dose information that specifies the X-ray dose acting on the patient using the dose distribution information.

17. A non-transitory electronically readable data storage medium comprising a computer program, which, when the computer program is executed on a computing device, causes the computing device to:
determine preliminary dose information that specifies a homogeneously distributed X-ray dose acting on a patient in an absence of a compensating filter arranged between the patient and an X-ray tube unit in an X-ray field that is configured to cause an inhomogeneous dose distribution in a plane perpendicular to a central ray of the X-ray field;
calculate dose distribution information using the preliminary dose information, wherein the dose distribution information specifies at least a dose distribution of an X-ray dose acting on the patient in a portion of the X-ray field covered by the compensating filter, and wherein the dose distribution information is calculated by a filter model that uses at least one filter parameter specifying the compensating filter and an arrangement of the compensating filter in the X-ray field; and
determine patient entrance dose information that specifies the X-ray dose acting on the patient using the dose distribution information.

* * * * *